(12) United States Patent
Matsuoka et al.

(10) Patent No.: US 6,440,588 B1
(45) Date of Patent: Aug. 27, 2002

(54) NITROGEN-CONTAINING HETEROCYCLIC COMPOUND AND ELECTROLUMINESCENT DEVICE

(75) Inventors: Masaru Matsuoka, Tenri; Koushi Fukunishi, Nara; Kazuko Shirai, Sakai; Koichi Takagi, Gobo; Toru Kitaguchi, Yokohama, all of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 63 days.

(21) Appl. No.: 09/711,293

(22) Filed: Nov. 14, 2000

(30) Foreign Application Priority Data

May 1, 2000 (JP) ........................ 2000-132508

(51) Int. Cl.$^7$ ...................... H05B 33/14; C07D 243/08
(52) U.S. Cl. .................. 428/690; 428/704; 428/917; 313/504; 313/506; 252/301.16; 540/575; 540/596; 540/604
(58) Field of Search ................ 428/690, 704, 428/917; 313/504, 506; 252/301.16; 540/553, 575, 596, 604

(56) References Cited

FOREIGN PATENT DOCUMENTS

JP          8-73443        3/1996

*Primary Examiner*—Marie Yamnitzky
(74) *Attorney, Agent, or Firm*—Birch, Stewart, Kolasch & Birch, LLP (57) ABSTRACT

A nitrogen-containing heterocyclic compound represented by the following formula (I) or (II):

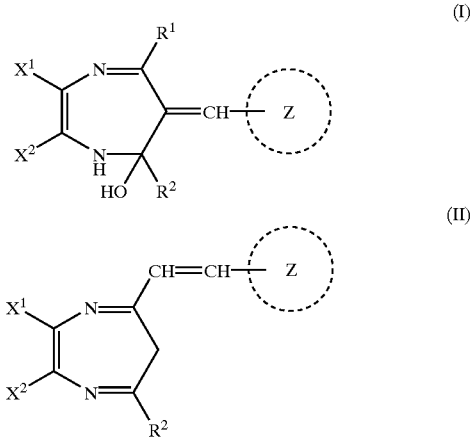

wherein $X^1$ and $X^2$ are the same or different, each representing a hydrogen atom, an alkyl group, or an electron attractive group and at least one of which being an electron attractive group; $R^1$ and $R^2$ are the same or different, each representing a hydrogen atom, an alkyl group, an aryl group, an aralkyl group, or an alkoxy group, and the ring Z represents a hydrocarbon ring which may have a substituent or a heterocycle which may have a substituent. The compound of the present invention is capable of emitting light or changing its color upon irradiation of light or under the action of an electric field.

15 Claims, 2 Drawing Sheets

NITROGEN-CONTAINING HETEROCYCLIC COMPOUND AND ELECTROLUMINESCENT DEVICE

FIELD OF THE INVENTION

The present invention relates to novel nitrogen-containing heterocyclic compounds useful as functional materials (particularly, materials for use in organic electroluminescence devices), a process for producing the same, and an organic electroluminescence device using the same.

BACKGROUND OF THE INVENTION

Conventionally, a variety of pigments or dyes (e.g., azo-, anthraquinone-, and phthalocyanine-type pigments) have been in use for dying or coloring fiber and others. These pigments or dyes, taken advantage of their characteristic of having a π-electron conjugate bond within a pigment molecule, have been utilized as, so called, functional pigments. So that these functional pigments have such functions as light-absorptivity (e.g., color, pleochroism), luminous radiation (fluorescent light), photoconductivity, and reversible changes by heat or light (thermochromism, photochromism), these have been used as functional materials in a variety of fields. For example, functional pigments that emit fluorescent light upon irradiation of light are used as fluorescent materials such as fluorescent dyes, fluorescent pigments, fluorescent flaw detecting agents, and fluorescent white dyes. Moreover, pigments that show photochromism have been applied for use in photochromic photos, photochromic materials (light-adjusting materials) for sunglasses, and others. Since photochromic compounds develop colors or fade as their molecular structure changes by the action of light, these compounds have been utilized also as rewritable optical recording materials. These recording materials have high image resolution and thus do not need to be developed in their coloring reaction.

Among these functional pigments mentioned above, in particular, those that emit light by the action (application) of electric fields are useful as emission center compounds for use in organic electroluminescence devices (hereinafter, occasionally abbreviated as organic EL device).

Conventionally, organic electroluminescence devices are composed of a compound or compounds having an electron-transporting function, a hole-transporting function, and an emission center function. There have been reported single-layered ones in which a single layer is provided with all the functions mentioned above, and multi-layered ones in which layers have different functions. Its principle of light emission is considered to be based on the phenomenon that electrons and holes injected from a pair of electrodes recombine within a light-emitting layer to form excitons, exciting an emission center compound forming a light-emitting layer.

Colors that organic EL devices emit can be selected by suitably choosing an emission center compound constituting the light-emitting layer. For example, Japanese Patent Application Laid-Open No. 73443/1996 (JP-A-8-73443) discloses the dimer of pyrazine in which a pyrazine group having a phenyl group is bound to a divalent aromatic group, and an organic EL device containing this pyrazine derivative. However, since this pyrazine dimer emits blue light of which the wavelength is relatively short, the electroluminescence device is limited in its emission wavelength and thus has greatly limited applications.

SUMMARY OF THE INVENTION

Thus, it is an object of the present invention to provide a compound capable of emitting light upon irradiation of light or by the action of electric fields and useful as a functional material such as an organic EL device-use material, a process for producing the same, and an organic EL device using the same.

Another object of the present invention is to provide a compound of which the emission wavelength is controllable over a wide range and capable of emitting light of longer wavelength (e.g., yellow to red light), and an organic EL device using the same.

The inventors of the present invention made intensive studies to achieve the above objects and finally found that a specific heterocyclic compound containing a nitrogen atom as a hetero atom emits light upon irradiation of light or by the action of electric fields and therefore is useful as such a functional material as those for organic electroluminescence devices. The present invention was accomplished based on the above findings.

That is, the nitrogen-containing heterocyclic compound of the present invention is represented by the following formula (I) or (II):

wherein $X^1$ and $X^2$ are the same or different, each representing a hydrogen atom, an alkyl group, or an electron attractive group and at least one of which being an electron attractive group; $R^1$ and $R^2$ are the same or different, each representing a hydrogen atom, an alkyl group, an aryl group, an aralkyl group, or an alkoxy group; and the ring Z is a hydrocarbon ring which may have a substituent or a heterocycle which may have a substituent.

The electron attractive group is at least one member selected from the group consisting of cyano group and acyl groups.

At least $X^1$ or $X^2$ may be a cyano group. $R^1$ and $R^2$ are the groups selected from the group consisting of alkyl groups and aryl groups. The ring Z may be an aromatic ring. The substituent of the ring Z is at least one member selected from the group consisting of alkyl groups, cycloalkyl groups, aryl groups, aralkyl groups, halogens atoms, and hydroxyl group. The compound is capable of emitting light by being irradiated with light. The compound is capable of emitting fluorescent light of which the wavelength is 380 to 800 nm. Moreover, the compound is capable of emitting light by the action of an electric field.

The present invention further includes a process for producing the above-mentioned compound (I) or (II).

The present invention further includes an organic electroluminescence device having, between a pair of electrodes, an organic layer (light-emitting layer) comprising a compound represented by the formula (I) or (II) shown above. The organic layer of this organic electroluminescence device may have (1) a single-layered structure composed of a light-emitting layer having at least one function selected from an electron-transporting function and a hole-transporting function, or (2) a multilayered structure (lamination) composed of a layer having at least one function selected from an electron-transporting function and a hole-transporting function, and a light-emitting layer. Moreover, the organic layer may comprise a compound represented by the above-shown formula (I) or (II) and an organic polymer having at least one function selected from an electron-transporting function and a hole-transporting function.

DETAILED DESCRIPTION OF THE INVENTION

The compound of the present invention (hereinafter, sometimes referred to as a nitrogen-containing heterocyclic compound) is represented by the following formula (I) or (II):

wherein $X^1$ and $X^2$ are the same or different, each representing a hydrogen atom, an alkyl group, or an electron attractive group and at least one of which being an electron attractive group; $R^1$ and $R^2$ are the same or different, each representing a hydrogen atom, an alkyl group, an aryl group, an aralkyl group, or an alkoxy group; and the ring Z represents a hydrocarbon ring which may have a substituent, or a heterocycle which may have a substituent.

Examples of the alkyl group are $C_{1-4}$ alkyl groups such as methyl and ethyl groups.

Exemplified as the electron attractive groups represented by $X^1$ and $X^2$ are cyano group, acyl groups (e.g., $C_{1-4}$ acyl groups, preferably $C_{1-3}$ acyl groups), and alkoxy groups (e.g., $C_{1-4}$ alkoxy groups, preferably $C_{1-2}$ alkoxy groups). As the electron attractive groups, cyano group is preferred.

Usually, at least one of $X^1$ and $X^2$ is a cyano group, and it is preferred that both of which are electron attractive groups (cyano groups). A nitrogen-containing heterocycle having such $X^1$ and $X^2$ (e.g., dicyanoazepine ring) seems to function as a coloring system upon intramolecular charge transfer.

Exemplified as the alkyl group represented by $R^1$ and $R^2$ are $C_{1-20}$ alkyl groups (for example, $C_{1-10}$ alkyl groups, preferably, $C_{1-6}$ alkyl groups, more preferably $C_{1-4}$ alkyl groups, particularly methyl and ethyl groups) such as methyl, ethyl, propyl, isopropyl, butyl, t-butyl, pentyl, hexyl, and octyl groups. Exemplified as the aryl group are $C_{6-20}$ aryl groups (preferably, $C_{6-18}$ aryl groups, more preferably $C_{6-14}$ aryl groups, particularly phenyl and naphthyl groups) such as phenyl, naphthyl, and biphenyl groups; examples of the aralkyl group are $C_{7-20}$ aralkyl groups (e.g., $C_{6-12}$aryl-$C_{1-8}$alkyl groups, preferably $C_{6-12}$aryl-$C_{1-6}$alkyl groups) such as benzyl and phenethyl groups; and examples of the alkoxy group are $C_{1-20}$ alkoxy groups (preferably $C_{1-10}$ alkoxy groups, more preferably $C_{1-6}$ alkoxy groups, particularly $C_{1-4}$ alkoxy groups) such as methoxy, ethoxy, propoxy, butoxy, and t-butoxy groups. Preferred groups are alkyl, aryl, and aralkyl groups. A compound of the formula (I) or (II) with $R^2$ being a bulky group of high steric hindrance [e.g., $C_{6-12}$ aryl groups such as phenyl and naphthyl groups, $C_{6-12}$aryl-$C_{1-4}$alkyl groups such as benzyl group, branched $C_{4-6}$alkyl groups such as t-butyl group], in many cases, seems to show the photochromism phenomenon, and this is probably due to large differences in energy between its structural isomers.

Although the hydrocarbon ring represented by the ring Z may be a non-aromatic hydrocarbon ring (e.g., $C_{3-20}$ cycloalkanes such as cyclohexane and cyclooctane, $C_{3-20}$ cycloalkenes such as cyclohexene), the ring Z is usually an aromatic hydrocarbon ring. The aromatic hydrocarbon ring need only have at least a benzene ring, example of which are benzene ring and condensed polycyclic aromatic hydrocarbon rings (e.g., naphthalene ring, anthracene ring, phenanthrene ring, phenalene ring). Preferred as the hydrocarbon ring are benzene, naphthalene, and phenalene rings.

Included among the examples of the heterocycle represented by the ring Z are heterocycles containing at least one hetero atom selected from nitrogen, oxygen, and sulfur atoms, and these may be condensed (ortho-condensed, ortho and peri-condensed) heterocycles of a plurality of heterocycles condensed together or of a heterocycle condensed with a hydrocarbon ring (non-aromatic hydrocarbon rings, or aromatic hydrocarbon rings), not limited to monocyclic heterocycles. Although it does not matter if the heterocycle represented by the ring Z is non-aromatic, it is usually aromatic.

Examples of the heterocycle having a nitrogen atom as a hetero atom are: a 5- or 6-membered monocyclic heterocycle such as pyrrole, imidazole, pyridine, and pyrazine rings; a condensed heterocycle being a hydrocarbon ring condensed with a 5- or 6-membered heterocycle such as indoline, quinoline, isoquinoline, quinazoline, carbazole, phenanthridine, acridine, and phenazine rings. As the heterocycle having an oxygen atom as a hetero atom, there are exemplified a 5- or 6-membered monocyclic heterocycle such as furan ring and a condensed heterocycle being a hydrocarbon ring condensed with a 5- or 6-membered heterocycle such as isobenzofuran ring and chromene ring. Included among the examples of the heterocycle having a sulfur atom as a hetero atom are a 5- or 6-membered monocyclic heterocycle such as thiophene ring; and a condensed heterocycle being a hydrocarbon ring condensed with a 5- or 6-membered heterocycle such as thianthrene ring. Exemplified as heterocycles having hetero atoms of different kinds are: a 5- or 6-membered monocyclic heterocycle such as morpholine, isothiazole, and isoxazole rings; and a condensed heterocycle being a hydrocarbon ring condensed with a 5- or 6-membered heterocycle such as phenoxathiin ring.

Preferred heterocycles include: an aromatic heterocycle such 5- or 6-membered heterocycles having a nitrogen atom as a hetero atom (e.g., pyrrole ring, pyridine ring); and an aromatic heterocycle (e.g., carbazole ring) being an aromatic hydrocarbon ring (particularly, benzene ring or naphthalene ring) condensed with a 5- or 6-membered heterocycle having at least a nitrogen atom as a hetero atom.

When the ring Z is a heterocycle containing an aromatic ring, the ring Z is usually bonded to the adjacent C=C bond at the aromatic ring constituting the ring Z to form a conjugated system. Moreover, in the case of a polycyclic ring, insofar as the ring Z is bonded via its aromatic ring, it does not matter whether the other ring or rings are non-aromatic or aromatic ones, and part of the ring Z (and part of the non-conjugated system) may be hydrogenated. As the hydrocarbon ring partially hydrogenated, there are mentioned hydrogenated naphthalene rings such as 1,2-dihydronaphthalene, 2,3-dihydrophenalene and 2,3,3a,4,5,6-hexahydrophenalene rings. Moreover, as the heterocycle partially hydrogenated, there are mentioned julolidine ring and 9-formyljulolidine ring.

The ring Z may have a variety of substituents, examples of which are alkyl groups (e.g., $C_{1-6}$alkyl groups typified by methyl and ethyl groups); cycloalkyl groups (e.g., $C_{3-10}$cycloalkyl groups); aryl groups (e.g., $C_{6-18}$aryl groups typified by phenyl group); arylalkyl groups (e.g., C6-12aryl-$C_{1-4}$alkyl groups typified by benzyl and diphenylmethyl groups); halogen atoms (fluorine, chlorine, bromine, and iodine atoms); hydroxyl group; alkoxy groups (e.g., $C_{1-6}$alkoxy groups such as methoxy and ethoxy groups); hydroxyalkyl groups (e.g., hydroxy$C_{1-6}$alkyl groups typified by hydroxymethyl group); carbonyl group; carboxyl group; alkoxycarbonyl groups (e.g., $c_{1-4}$alkoxycarbonyl groups); alkylcarbonyl groups (e.g., $C_{1-6}$alkyl-carbonyl groups); arylcarbonyl groups (e.g., $C_{6-12}$aryl-carbonyl groups); acyloxy groups (e.g., $C_{1-6}$acyloxy groups typified by acetyloxy group); cyano group; amino group; N-substituted amino groups (e.g., mono- or di$C_{1-6}$alkylamino groups typified by methylamino, dimethylamino, diethylamino, and methylethylamino groups, mono- or di$C_{6-18}$arylamino groups typified by phenylamino group, $C_{1-6}$acylamino groups typified by acetamide group); nitro group; and sulfonyl group.

Preferred substituents include $C_{1-4}$alkyl groups, $C_{6-12}$aryl groups, hydroxyl group, $C_{1-4}$alkoxy groups, amino group, mono- or di$C_{1-6}$alkylamino groups, mono- or di$C_{6-18}$arylamino groups, $C_{1-4}$acyloxy groups, and $C_{1-4}$acylamino groups. As the substituent(s), an electron donative group (e.g., amino group, N-substituted amino group) seems to be preferable.

There is no particular restriction as to the position(s) of the substituent(s) on the hydrocarbon ring or the heterocycle. For example, on the benzene ring, the substituent(s) is/are in the o-, m-, or p-position, and usually in the o- and/or p-position. Moreover, the hydrocarbon ring and the heterocycle each may have a plurality of substituents.

Exemplified as a hydrocarbon ring having such substituent(s) are benzene rings having a substituent(s) (e.g., benzene rings substituted with at least one member selected from hydroxyl group, a $C_{1-4}$alkoxy group, amino group, and a mono- or di$C_{1-4}$alkyl-substituted amino group). Moreover, exemplified as the heterocycle having a substituent(s) is an N-substituted heterocycle in which its hetero atom(s) (e.g., nitrogen atom) is substituted with a $C_{1-6}$alkyl group [e.g., carbazole ring substituted with an N-$C_{1-4}$alkyl group].

In the formula (I) or (II), examples of combinations of substituents are exemplified below.

$X^1$: cyano group $X^2$: cyano group $R^1$: a $C_{1-4}$alkyl or $C_{6-12}$aryl group $R^2$: a $C_{1-4}$alkyl $C_{6-12}$aryl, $C_{1-6}$alkoxy, or $C_{7-20}$aralkyl group Z: an aromatic ring [e.g., a benzene ring having a substituent (at least one member selected from hydroxyl group, a $C_{1-4}$alkoxy group, amino group, and N-substituted amino group); a condensed polycyclic hydrocarbon ring; or a polycyclic aromatic heterocycle of a hetero cycle condensed with an aromatic hydrocarbon ring] or its partially hydrogenated ring.

Particularly preferred as the compound (I) or (II) is a diazepine ring-containing compound.

Typical examples of the compound represented by the formula (I) are compounds in which the ring Z is a benzene ring which may have a substituent [e.g., 2,3-dicyano-5-phenyl-5-hydroxy-6-phenylmethylidene-7-methyl-4H-1,4-diazepine; 2,3-dicyano-5-phenyl-5-hydroxy-6-(4-$C_{1-4}$alkoxyphenylmethylidene)- 7-methyl-4H-1,4-diazepine such as 2,3-dicyano-5-phenyl-5-hydroxy-6-(4-methoxyphenylmethylidene)-7-methyl-4H-1,4-diazepine; 2,3-dicyano-5-phenyl-5-hydroxy-6-(4-mono or di$C_{1-4}$alkylaminophenylmethylidene)-7-methyl-4H-1,4-diazepines such as 2,3-dicyano-5-phenyl-5-hydroxy-6-(4-dimethylaminophenylmethylidene)-7-methyl-4H-1,4-diazepine; those with phenyl group in the 5-position substituted by a $C_{1-4}$alkyl group, a $C_{7-16}$aralkyl group, or a $C_{1-6}$alkoxy group]; compounds in which the ring Z is a condensed polycyclic hydrocarbon ring or its partially hydrogenated ring [e.g., 2,3-dicyano-5-phenyl-5-hydroxy-6-(naphthalen-2-yl-methylidene)-7-methyl-4H-1,4-diazepine, 2,3-dicyano-5--phenyl-5-hydroxy-6-(phenalen-2-yl-methylidene)-7-methyl-4H-1,4-diazepine]; and compounds in which the ring Z is an aromatic heterocycle of a heterocycle condensed with an aromatic hydrocarbon ring, or its partially hydrogenated ring [e.g., a 2,3-dicyano-5-phenyl-5-hydroxy-7-methyl-4H -1,4-diazepine in which a heterocycle being a 5- or 6-membered heterocycle having a nitrogen atom as a hetero atom condensed with an aromatic hydrocarbon ring is bonded at the 6-position (e.g., 2,3-dicyano-5-phenyl-5-hydroxy-6-(9-ethyl-3-carbazolylmethylidene)-7-methyl-4H-1,4-diazepine)].

Exemplified as the typical compound represented by the formula (II) are: 2,3-dicyano-5-phenyl-7-(2-phenylvinyl-1-yl)-6H-1,4-diazepine; 2,3-dicyano-5-phenyl-7-(2-(4-$C_{1-4}$alkoxyphenyl)vinyl-1-yl)-6H-1,4-diazepines such as 2,3-dicyano- 5-phenyl-7-(2-(4-methoxyphenyl)vinyl-1-yl)-6H-1,4-diazepine; 2,3-dicyano-5-phenyl-7-(2-(4-mono- or di$C_{1-4}$alkylaminophenyl)vinyl-1-yl)-6H-1,4-diazepines such as 2,3-dicyano-5-phenyl-7-(2-(4-dimethylaminophenyl)vinyl-1-yl)-6H-1,4-diazepine; those with the phenyl group in the 5-position substituted with a $C_{1-4}$alkyl group, a $C_{7-16}$aralkyl group, or a $C_{1-6}$alkoxy group]; compounds in which the ring Z is a condensed polycyclic hydrocarbon ring or its partially hydrogenated ring [e.g., 2,3-dicyano-5-phenyl-7-(2-(phenalen-2-yl)vinyl-1-yl)-6H-1,4-diazepine]; and compounds in which the ring Z is an aromatic heterocycle of a heterocycle condensed with an aromatic hydrocarbon ring, or its partially hydrogenated ring [e.g., 2,3-dicyano-5- phenyl-7-methyl-6H-1,4-diazepine in which a vinyl group having a condensed heterocyclic group being a 5- or 6-membered heterocyclic group containing a nitrogen atom as a hetero atom condensed with an aromatic hydrocarbon ring is bonded at the 7-position (e.g., 2,3-dicyano-5-phenyl-7-[(9-ethyl-3-carbazolyl)vinyl-1-yl]-6H-1,4-diazepine)].

[Production Process]

The compound of the present invention can be prepared in accordance with the following reaction formula (1).

wherein $X^1$, $X^2$, $R^1$, $R^2$, and the ring Z have the same meanings as defined above.

The compound of the formula (I) or (II) can be obtained by reacting the compound represented by the formula ($I_a$) or ($II_a$) (including its structural isomers) with the compound represented by the formula (III). Probably due to the C=C double bond in the nitrogen-containing heterocycle of the compound of the formula (I) or (II) isomerized into an enamine, it is possible to react the compound of the formula ($I_a$) or ($II_a$) with an aldehyde (III) efficiently.

Typical examples of the compound represented by the formula (III) are aldehydes [e.g., aldehydes in which the ring z is a benzene ring (e.g., benzaldehyde, halobenzaldehyde, aminobenzaldehyde, N-substituted aminobenzaldehyde, phenolaldehyde, $C_{1-4}$alkoxybenzaldehyde); aldehydes in which the ring Z is a condensed polycyclic hydrocarbon ring (e.g., naphthalenecarbaldehyde, phenalenecarbaldehyde); aldehydes in which the ring Z is a 5- or 6-membered heterocycle containing a nitrogen atom as a hetero atom, or a condensed heterocycle of a heterocycle and a hydrocarbon ring (9-ethyl-3-formylcarbazole)]. The amount of the compound represented by the formula (III) is, per 1 mol of the compound of the formula ($I_a$) or ($II_a$), about 1 to 3 mol, preferably about 1 to 1.5 mol.

The reaction described above may be carried out in the presence of a solvent inert to the reaction, such as an aliphatic hydrocarbon (e.g., hexane), an alicyclic hydrocarbon (e.g, cyclohexane), an aromatic hydrocarbon (e. g., benzene, toluene), a halogenated hydrocarbon (e.g., chloroform), an alcohol (e.g., methanol, ethanol, isopropyl alcohol, butanol), an ester (e.g., ethyl acetate, butyl acetate, isobutyl acetate), an ether (e. g., dioxane, diethyl ether, teterahydrofuran), an amide (formamide, acetamide, dimethylformamide (DMF), dimethylacetamide), a nitrile (e.g., acetonitrile, benzonitrile), a sulfoxide (e.g., dimethyl sulfoxide). If necessary, a catalyst (e.g., a basic catalyst such as pyridine and piperidine may be used). The amount of the catalyst to be used can be selected within the range of, per 1 mol of the compound of the formula ($I_a$) or ($II_a$), about 0.001 to 1 mol.

When a solvent is used, the reaction temperature can be selected within the range of about 0° C. to reflux temperature and is for example about 50 to 120° C., preferably 60 to 100° C. The reaction can be effected under ordinary pressure, reduced pressure, or applied pressure. The reaction may be carried out in an atmosphere of an inert gas (e.g., nitrogen, argon, helium).

After the reaction, the compound (I) or (II) formed in the above-described reaction can easily be separated and purified by such a conventional means as filtration, condensation, distillation, extraction, crystallization, recrystallization, column chromatography, or a combination means thereof.

The compound represented by the formula (Ia) or (IIa) may be prepared also in accordance with the following reaction formula (2).

wherein $X^1$, $X^2$, $R^1$, and $R^2$ have the same meanings as defined above.

The compound of the formula ($I_a$) can be formed by reacting (condensing) the compound represented by the formula (IV) with the compound represented by the formula (V). The compound of the formula ($II_{a1}$) can be obtained by, if necessary, dehydrating the compound of the formula ($I_a$)

The compound of the formula ($II_a$) corresponds to the compound of the formula ($II_{a1}$) with methyl group as $R^1$.

Typical examples of the compound represented by the formula (IV) are diamines [e.g., 1,2-dicyano-1,2-diaminoethene(diaminomaleonitrile), 1-cyano-2-(dimethylamino)-1,2-diaminoethene, 1,2-dicyano-2-(benzylamino)-1-aminoethene)]. Typical examples of the compound represented by the formula (V) are diketone compounds ([e.g., 1,3-diketones such as acetylacetone, benzoylacetone, dibenzoylmethane].

The amount of the compound of the formula (V) to be used is usually about 1 to 3 mol, preferably about 1 to 1.5 mol relative to 1 mol of the compound of the formula (IV).

The condensation reaction described above may be effected in the presence or absence of a catalyst. Exemplified as the catalyst are conventional ones, such as acid catalysts (e.g., inorganic acids such as sulfuric acid, phosphoric acid, hydrochloric acid; organic acids such as acetic acid, sulfonic acid, p-toluenesulfonic acid) and basic catalysts (e.g., hydroxides or oxides of alkaline or alkaline earth metals). The amount of the catalyst to be used can be selected within the range of about 0.001 to 1 mol relative to 1 mol of the compound of the formula (IV). A dehydrating agent (e.g., phosphorus pentoxide) may additionally be used.

The condensation reaction may be effected in a solvent inert to the reaction. As the solvent, those listed above are available (e.g., benzene). When a solvent is used, the reaction temperature can be selected within the range of about 0° C. to reflux temperature, and is for example about 50 to 120° C., preferably about 60° C. to 100° C. It is possible to effect the reaction under ordinary, reduced, or applied pressure. The reaction may be effected in an atmosphere of an inert gas (e.g., nitrogen, argon, helium). After the reaction, the compound formed by the condensation reaction described above can easily be separated and purified by any separating means of those mentioned above.

The compound of the present invention is characterized in that, due to its specific structure represented by the formula (I) or (II), it is capable of emitting light by being supplied with energy externally (irradiation of light, the action of an electric field). There is no particular restriction as to the irradiation of light so far as light is of a certain wavelength capable of exciting the nitrogen-containing heterocyclic compound of the formula (I) or (II). For example, ultraviolet rays (400 nm or less) and visible rays (e.g., 360 to 860 nm (particularly, 400 to 760 nm, 400 to 650 nm)), particularly visible rays, can be used. The emission wavelength varies over a wide range (e.g., about 380 to 900 nm, preferably about 380 to 800 nm, more preferably about 400 to 700 nm (violet to red)), depending on, for example, the kind(s) of the substituent(s) and the position of substitution. The nitrogen-containing heterocyclic compound (I) or (II) of the present invention presents, though varies for different kinds of substituents or positions of substitution, violet to red color (particularly, yellow to red) and has a large molar absorption coefficient. This may be because the composition is a color (developing) system of the intramolecular charge transfer type in which the nitrogen-containing heterocycle within its molecule and the aromatic ring being the ring Z act as an electron attractive group (acceptor) and an electron donative group, respectively.

Upon irradiation of light (particularly, visible rays), the compound of the formula (I) or (II) emits fluorescent light in a solution. The wavelength of fluorescence varies within the range mentioned above. Particularly, although the nitrogen-containing heterocycle of the compound of the present invention has a non-planar structure, generally, it seems to have a tendency to emit fluorescent light of relatively long wavelengths (about 500 to 700 nm, preferably about 530 to 700 nm: yellow to red), probably because the heterocycle acts as a strong electron-withdrawing group.

Under the action of an electric field (injection of a carrier), the compound of the present invention is capable of emitting light. The emission wave length can be selected within the range mentioned above. Moreover, the compound of the present invention is capable of emitting light of relatively long wavelengths (about 500 to 700 nm, preferably 550 to 700 nm: yellow to red). Therefore, the compound of the present invention is useful as an emission center compound for an organic EL device.

Moreover, the compound of the formula (I) or (II) contained in a solid (e.g., a thin film on which the composition is vapor-deposited) shows the same properties (emission of light upon irradiation of light or by the action of an electric field) as those shown in the case of the compound being in a solution. Therefore, the composition of the present invention can be used also in a solid state (e.g., as a film, powder, particles), and its use is not restricted.

So that the compound of the present invention is capable of emitting light upon irradiation of light or by the action of an electric field, it can be utilized in various fields as a functional material. For example, the compound of the present invention is useful not only as a fluorescent material (e.g., a fluorescent pigment, a fluorescent flaw detecting agent, a fluorescent white dye, particularly as a fluorescent material such as a fluorescent dye) but also as a material for display devices (e.g., light emitting device material such as a material such as an electroluminescence material).

[Organic Electroluminescence Device]

The electroluminescence device (EL) device of the present invention is composed of a pair of electrodes and an organic layer interposed therebetween. The organic layer comprises at least the compound represented by the aforementioned formula (I) or (II). Particularly, the layer containing the compound of the formula (I) or (II) forms a light-emitting region, constituting a light-emitting layer. The light-emitting layer may be formed of a film-formable compound of the formula (I) or (II) singly, or of a film-formable or non-formable compound and a binder having a film-forming properties. As the binder, a resin having a film-forming properties (a thermoplastic resin, a thermosetting resin) can be used.

Examples of the thermoplastic resin are olefinic resins such as polyethylene, polypropylene, ethylene-propylene copolymer, and polybutene; styrenic resins such as polystyrene, rubber-modified polystyrene (HIPS), acrylonitrile-styrene copolymer, and acrylonitrile-butadiene-styrene copolymer; acrylic resins [e.g., homo- or copolymers of (meth)acrylic monomers (e.g., $C_{1-6}$alkyl (meth)acrylates such as methyl (meth)acrylate, ethyl (meth)acrylate, and butyl (meth)acrylate; hydroxy$C_{2-4}$alkyl (meth)acrylates such as hydroxyethyl (meth)acrylate and hydroxypropyl (meth)acrylate; glycidyl (meth)acrylate; (meth)acrylic acid; (meth)acrylonitrile); copolymers of the (meth)acrylic monomers mentioned above with copolymerizable monomers (e.g., aromatic vinyl monomers such as styrene) (e.g.,methyl methacrylate-styrene copolymer)]; vinyl-series resins such as vinyl alcohol-series polymers typified by polyvinyl alcohol and ethylene-vinyl alcohol copolymer, polyvinyl chloride, vinyl chloride-vinyl acetate copolymer, polyvinylidene chloride, polyvinyl acetate, ethylene-vinyl acetate copolymer, and polyvinylacetyl; polyamide-series resins such as 6-nylon, 6,6-nylon, 6,10-nylon, and 6,12-nylon; polyester resins [e.g., polyalkylene terephthalates (e.g., polyethylene terephthalate, polybutylene terephthalate), alkylene arylate-series resins such as polyalkylene naphthalate, alkylene arylate copolyester resins]; fluorine-containing resins; polycarbonate; polyacetal; polyphenylene ether; polyphenylene sulfide; polyether sulfone; polyether ketone; thermoplastic polyimide; thermoplastic polyurethane; and norbornene-series polymer.

Exemplified as the thermosetting resin are phenolic resins, urea resins, meramine resins, thermosetting acrylic resins, unsaturated polyester resins, alkyd resins, diallyl phthalate resins, epoxy resins, and silicone resins.

These binders can be used either singly or in combination.

The content of the compound of the formula (I) or (II) is, per 100 parts by weight of the binder, about 0.01 to 10 parts by weight, preferably about 0.05 to 5 parts by weight, more preferably about 0.1 to 3 parts by weight.

If necessary, into the light-emitting layer may be incorporated other emission center compounds, examples of which are heterocyclic compounds containing at least one hetero atom selected from oxygen, nitrogen, and sulfur atoms [e.g., bis($C_{1-6}$alkyl-benzoxazoyl)thiophene typified by 2,5-bis(5-tert-butyl-2-benzoxazoyl)-thiophene; nile red; coumarins typified by coumarin 6 and coumarin 7; 4-(dicyano$C_{1-4}$alkylene)-2-$C_{1-4}$alkyl-6-(p-di$C_{1-4}$alkylaminostyryl)-4H-pyran typified by 4-(dicyanomethylene)-2-methyl-6-(p-dimethylaminostyryl)-4H-pyran; and quinacridone]; condensed polycyclic hydrocarbons such as rubrene and perylene; tetra$C_{6-12}$aryl-1,3-butadiene such as 1,1,4,4-tetraphenyl-1,3-butadiene (TPB); bis(2-(4-$C_{1-4}$alkylphenyl) $C_{2-4}$alkynyl)benzene such as 1,4-bis(2-(4-ethylphenyl) ethynyl)benzene; and bis(2,2'-di$C_{6-12}$arylvinyl)biphenyl such as 4,4'-bis(2,2'-diphenylvinyl)biphenyl. Of these, nile red and coumarin 6 are preferable. These emission center compounds can be used either singly or in combination. The content of the emission center compound is selected within a range not adversely affecting the efficiency of emission of the compound (I) or (II) and about 0.01 to 10 parts by weight, about 0.05 to 5 parts by weight, more preferably about 0.1 to 3 parts by weight relative to 100 parts by weight of the binder. The proportion of the compound of the formula (I) or (II) to the other emission center compound(s) is about 40/60 to 100/0, preferably about 50/50 to 95/5, more preferably about 60/40 to 90/10.

If necessary, the light-emitting layer comprising the compound of the formula (I) or (II) may be given an electron-transporting function and/or a hole-transporting function. For the purpose of giving such function(s), (1) to the light-emitting layer may be added organic polymers or compounds having the functions described above; or (2) the light-emitting layer may be laminated with a layer or layers having the functions described above. In the case (1), it is possible to fabricate an organic electroluminescence device having a single-layered structure.

Exemplified as the organic polymer having at least one function selected from the electron-transporting and hole-transporting functions are vinyl-series polymers having at least one functional group selected from hole-transporting functional groups and electron-transporting functional groups in the main chain or a side chain, such as polyphenylenevinylenes [e.g., homo- or copolymers of $C_{6-12}$aryleneviniylenes which may have a substituent (e.g., $C_{1-10}$alkoxy group), such as polyphenylenevinylene, poly(2, 5-dimethoxyphenylenevinylene, and polynaphthalenevinylene]; polyphenylenes (e.g., polyparaphenylene) [e.g., homo- or copolymers of phenylenes which may have a substituent (e.g., $C_{1-10}$ alkoxy groups), such as polyparaphenylene and poly-2,5-dimethoxyparaphenylene; polythiophenes [e.g., poly$C_{1-20}$alkylthiophenes such as poly(3-alkylthiophene); poly$C_{3-20}$cycloalkylthiophenes such as poly(3-cyclohexylthiophene); homo- or copolymers of $C_{6-20}$arylthiophenes which may have a substituent (e.g., $C_{1-10}$alkyl groups) such as poly(3-(4-n-hexylphenyl) thiophene); polyfluorenes such as poly$C_{1-20}$alkylfluorenes; vinyl-series polymers having at least one functional group selected from a hole-transporting functional group and an electron-transporting functional group in the main or side chain, such as poly-N-vinylcarbazole (PVK), poly-4-N,N-diphenylaminostyrene, poly(N-p-diphenylamino) phenylmethacrylamide), poly(N,N'-diphenyl-N,N'-bis(3-methylphenyl)-1,1'-biphenyl-4,4'-diaminomethacrylamide) (PTPDMA), and poly-4-(5-naphthyl-1,3,4-oxadiazole) styrene; poly$C_{1-4}$alkylphenylsilanes such as polymethylphenylsilane; polymers having an aromatic amine derivative in the side or main chain; and copolymers thereof. These organic polymers can be used either singly or in combination. Particularly preferred are homo- or copolymers of which the main component (e.g., 50 to 100% by weight) is N-vinylcarbazole (e.g., copolymers of those with copolymerizable monomers such as (meth)acrylic monomers, styrenic monomers, and vinyl ester-series monomers) and aromatic amine derivatives.

PVK is amorphous and excellent in heat resistance (glass transition temperature Tg: 224° C.). Although there is no particular restriction on the degree of polymerization, it is for example about 100 to 1,000, preferably about 200 to 800.

In the case where the light-emitting layer is comprised of the compound of the formula (I) or (II) and the organic polymer described above, the content of the compound of the formula (I) or (II) is, per 100 parts by weight of the organic polymer, about 0.01 to 10 parts by weight, preferably about 0.05 to 5 parts by weight, more preferably about 0.1 to 3 parts by weight.

If necessary, to the light-emitting layer comprised of the compound of the formula (I) or (II) and the organic polymer may be added a compound having an electron- or hole-transporting function.

Examples of the compound having an electron-transporting function are oxadiazole derivatives [e.g., oxadiazole derivatives having a $C_{6-12}$aryl group which may have a substituent, such as 2-(4-biphenyl)-5-(4-tert-butylphenyl)-1,3,4-oxadiazole (PBD), 2,5-bis(1-naphtyl)-1, 3,4-oxadiazole (BND), 1,3-bis[5-(4-tert-butylphenyl)-1,3, 4,-oxadiazole)]benzene (BPOB), 1,3,5-tris[5-4-tert-butylphenyl)-1,3,4-oxadiazole]benzene (TPOB), and 1,3,5-tris[5-(1-naphtyl)-1,3,4-oxadiazole]benzene (TNOB); diphenoquinones [e.g., diphenoquinones which may have a substituent (e.g., $C_{1-10}$ alkyl groups), such as 3,5,3',5'-tetrakis-tert-butyldiphenoquione; 1,2,3,4,5-pentaphenyl-1, 3-cyclopentadiene (PPCP); and quinolinic acid complexes such as tris(8-quinolinorato)aluminium (III) complex, bis (benzoquinolinorato)beryllium complex, and tris(10-hydroxybenzo[h]quinolilate)beryllium complex, with oxadiazole derivatives (e.g., PBD) particularly preferred.

As the compound having a hole-transporting function, there may be exemplified aromatic tertiary amines such as N,N'-diphenyl-N,N'-bis(3-methylphenyl)-1,1'-biphenyl-4, 4'-diamine (TPD), N,N'-diphenyl-N,N'-bis(1-naphthyl)-1,1'-biphenyl-4,4'-diamine (NPD), 1,1-bis[(di-4-tolylamino) phenyl]cyclohexane, N,N,N'N'-tetra(3-methylphenyl)-1,3-diaminobenzene (PDA), 4,4',4"-tris(3-methylphenylphenylamino)triphenylamine (m-MTDATA), 4,4',4"-tris(1-naphthylphenylamino)triphenylamine(1-

TNATA), 4,4',4"-tris(2-naphthylphenylamino) triphenylamine (2-TNATA), 4,4',4"-tri(N-carbazolyl) triphenylamine (TCTA), 1,3,5-tris[4-(3-methylphenylphenylamino)phenyl]benzene (m-MTDAPB), and triphenylamine; and phthalocyanines.

The compounds having an electron-transporting function and those having a hole-transporting function may be used either singly or in combination.

The content of the compound having en electron and/or hole-transporting function is, relative to 100 parts by weight of the binder (and/or the organic polymer described above), about 10 to 200 parts by weight, preferably about 30 to 150 parts by weight, more preferably about 50 to 130 parts by weight.

When the light-emitting layer is lacking in either the electron-transporting function or attempting to improve each function, a layer or layers having the desired function may be applied onto the light-emitting layer by a conventional method (e.g., vapor deposition, solution coating). These layers may be of low molecular weight compounds or high molecular weight compounds.

The thickness of each layer constituting the organic layer is not particularly limited, and is for example about 1 nm to 1 μm, preferably about 5 to 800 nm, more preferably about 10 to 500 nm, particularly about 15 to 300 nm.

As the anode of the organic EL device, for example, a transparent electrode (e.g., indium-tin-oxide (ITO) electrode) formed by a conventional process (e.g., vacuum deposition) is employed. As the cathode, a highly conductive metal of low work function (e.g., magnesium, lithium, aluminum, silver) is used. In the case where magnesium is employed as the cathode, for improving the adhesion to a film for organic EL devices, magnesium may be deposited together with a small amount of silver (e.g., 1 to 10% by weight).

There is no particular restrictions on the process for the production of the organic electroluminescence device of the present invention, and conventional ones are adoptable. For example, the organic layer (e.g., light-emitting layer) is formed by forming a coat being the aforementioned transparent electrode (e.g., ITO electrode) on a transparent substrate and then applying or casting a coating fluid comprising the compound of the formula (I) or (II) in a conventional manner (e.g., spin coating, casting). The organic electroluminescence device is fabricated by further forming a cathode on the organic layer by vapor deposition or other means. If necessary, the anode or the light-emitting layer may be laminated with a layer or layers having an electron- and/or hole-transmitting function by such a conventional method as vapor deposition or coating.

Examples of the substrate are those transparent enough to transmit light emitted by the emission center compound (e.g., plates of soda glass, non-alkali glass, or quartz glass and sheets or films of polymers such as polyester, polysulfone, polyethersulfone). When fabricating a flexible organic EL device, the use of a polymer film is preferred.

Although the thickness of the organic EL device (e.g., the organic layer plus the electrodes) as a whole is not particularly limited, it is about 50 nm to 10 μm, preferably about 100 nm to 8 μm, more preferably about 300 nm to 5 μm.

According to the present invention, since a nitrogen-containing heterocyclic compound having a specific structure is employed as the organic layer (particularly, light-emitting layer) of the organic EL device, it is possible to control the wavelength of light the organic EL device emits. Moreover, according to the present invention, in spite of the fact that the nitrogen-containing heterocyclic compound has a non-planar structure, the compound can emit light of relatively long wavelength (e.g., about 530 to 700 nm, yellow to red) and provides an organic EL device of high luminance and high durability.

The compound of the present invention can emit light by being irradiated with light or by the action of an electric field because it has a specific nitrogen-containing heterocycle. Therefore, the compound of the present invention is useful as a functional material typified by a fluorescent material and a material for display devices. Since a compound which emits light by the action of an electric field is particularly useful as an emission center compound for use in an organic electroluminescenet device and is capable of emitting light within a wide wavelength range, it is possible to control the wavelength of light to be emitted by an organic EL device.

EXAMPLES

The following example are intended to show the invention in further detail and should by no means be construed as defining the scope of the invention.

Example 1

In the presence of a catalytic amount of HCl (4N=4 mol/l), 1 mol of diaminomaleonitrile was reacted with 1 mol of benzoylacetone in a solvent (benzene) at 45° C. for 6 hours to give 2,3-dicyano-5-hydroxy-5-phenyl-7-methyl-4H-1,4-diazepine (compound 1a). The diazepine compound (1a) thus obtained was reacted with 4-methoxybenzaldehyde in the presence of piperidine to give the object compound 2,3-dicyano-5-hydroxy-5-phenyl-6-(4-methoxyphenylmethylidene)-7-methyl-4H-1,4-diazepine (compound 1).

The compound (1) was dissolved in a solvent ($CHCl_3$) and its absorption spectrum and fluorescence spectrum were measured. The peak wavelength in the absorption spectrum was 447 nm, and that in the fluorescence spectrum was 512 nm, the difference between which was 65 nm.

Example 2

The object compound 2,3-dicyano-5-hydroxy-5-phenyl-6-(4-diethylaminophenylmethylidene)-7-methyl-4H-1,4-diazepine (compound 2) was obtained in the same manner as in Example 1 with the exception that 4-diethylaminobenzaldehyde was used in lieu of 4-methoxybenzaldehyde. As in Example 1, the absorption spectrum and the fluorescence spectrum of the compound (2) thus obtained were measured. The peak wavelength in the absorption spectrum was 528 nm, and that in the fluorescence spectrum was 580 nm, the difference between which was 52 nm.

Example 3

The object compound 2,3-dicyano-5-hydroxy-5-phenyl-7-methyl-6-(julolidin-9-yl-methylidene)-4H-1,4-diazepine (compound 3) represented by the following formula (ii) was obtained (yield: 50%) in the same manner as in Example 1 with the exception that an aldehyde represented by the formula (i) was used in lieu of 4-methoxybenzaldehyde.

As in Example 1, the absorption spectrum and the fluorescence spectrum of the compound (3) thus obtained were measured. The peak wavelength in the absorption spectrum was 554 nm, and that in the fluorescence spectrum was 614 nm, the difference between which was 60 nm.

Compound 3

NMR (CDCl$_3$): 1.99 (4H, m, 2CH$_2$), 2.51 (3H, s, CH$_3$), 2.84 (4H, J=5.4 Hz, 2CH$_2$), 3.34 (4H, t, J=5.4 Hz, 2CH$_2$), 6.07 (2H, s, 2CH), 7.36 (2H, s, phenyl protons), 7.45 (3H, t, J=7.5 Hz, phenyl protons), 7.96 (2H, d, J=7.5 Hz, phenyl protons), 8.26 (1H, s, OH), 14.06 (1H, broad, NH)

Example 4

The object compound 2,3-dicyano-5-hydroxy-5-ethoxy-6-(4-diethylaminophenylmethylidene)-7-methyl-4H-1,4-diazepine (compound 4) was obtained in the same manner as in Example 1 with the exception that ethoxycarbonylacetone and 4-diethylaminobenzaldehyde were used in lieu of benzoylacetone and 4-methoxybenzaldehyde, respectively. As in Example 1, the absorption spectrum and the fluorescence spectrum of the compound (4) thus obtained were measured. The peak wavelength in the absorption spectrum was 499 nm, and that in the fluorescence spectrum was 543 nm, the difference between which was 44 nm.

Compound 4

NMR (CDCl$_3$): 11.971 (s, 1H, NH), 8.325 (s, 1H, OH), 7.900 (d, 2H, J=9.0 Hz, phenyl protons), 6.694 (d, 2H, J=9.0 Hz, phenyl protons), 4.966 (s, 1H, CH), 4.252 (q, 2H, J=7.2 Hz, CH$_2$), 2.384 (s, 3H, CH$_3$), 1.324 (t, 3H, J=7.2 Hz, CH$_3$), 1.232 (t, 6H, J=7.2 Hz, 2CH$_3$)

Example 5

In the presence of a catalytic amount of acetic acid, 2,3-dicyano-5-hydroxy-5-phenyl-7-methyl-4H-1,4-diazepine (compound 5a) was obtained by reacting 1 mol of diaminomaleonitrile with 1 mol of acetylacetone in a solvent (benzene) at 45° C. for 6 hours. The diazepine compound (5a) thus obtained was dehydrated in the presence of phosphorus pentoxide. The object compound 2,3-dicyano-5-phenyl-7-(2-(4-methoxyphenyl)vinyl-1-yl)-6H-1,4-diazepine (compound 5) was obtained by reacting the diazepine compound (5b) thus obtained with 4-methoxybenzaldehyde in the presence of piperidine.

The absorption spectrum and the fluorescence spectrum of the compound (5) thus obtained were measured in the same manner as in Example 1. The peak wavelength in the absorption spectrum was 390 nm and that in the fluorescence spectrum was 438 nm, the difference between which was 48 nm.

Compound 5b

NMR (CDCl$_3$): 8.010 (dd, 2H, J=8.2 Hz, phenyl protons), 7.616 (m, 1H, phenyl protons), 7.558 (m, 2H, phenyl protons), 5.057 (d, 1H, J=10 Hz, CH$_2$), 2.220 (s, 3H, CH$_3$), 1.870 (d, 1H, J=10 Hz, CH$_2$)

Compound 5

NMR (CDCl$_3$): 8.003 (dd, 2H, J=8.3, 1.5 Hz, phenyl protons), 7.513 (d, 1H, J=15.6 Hz, CH), 7.509 (m, 3H, phenyl protons), 7.433 (d, 2H, J=9.0 Hz, phenyl protons), 6.893 (d, 2H, J=9.0 Hz, phenyl protons), 6.683 (d, 1H, J=15.9 Hz, CH), 5.365 (broad, 1H, CH$_2$), 3.833 (s, 3H, OCH$_3$), 1.919 (broad, 1H, CH$_2$)

Examples 6 to 11

The object compound represented by the following formula (v) was obtained in the same manner as in Example 5 with the exception that a compound represented by the following formula (iii) and a compound represented by the following formula (iv) were used in lieu of 2,3-dicyano-5-phenyl-7-methyl-6H-1,4-diazepine and 4-methoxybenzaldehyde, respectively. The groups employed as R$^3$ and the ring Z in the formulae (iii) (iv) (v) are shown in Table 1. The absorption spectrum and the fluorescence spectrum of the object compound thus obtained were measured as in Example 5. The results are shown in Table 1.

(v)

| | R³ | Z | λ max(nm) | Fmax(nm) | Fmax-λ max(nm) |
|---|---|---|---|---|---|
| Ex. 6 | methyl | dimethylaminophenyl | 477 | 581 | 104 |
| Ex. 7 | phenyl | dimethylaminophenyl | 500 | 615 | 115 |
| Ex. 8 | methyl | diethylaminophenyl | 491 | 588 | 97 |
| Ex. 9 | phenyl | diethylaminophenyl | 510 | 620 | 110 |
| Ex. 10 | methyl | 9-julolidinyl | 519 | 616 | 97 |
| Ex. 11 | phenyl | 9-julolidinyl | 542 | 649 | 107 |

The NMR data of the compounds obtained in Examples 6 to 11 are shown below.

Compound Obtained in Example 6

NMR (CDCl₃): 7.469 (d, 2H, J=9.0 Hz, phenyl protons), 7.455 (d, 1H, J=17.4 Hz, CH), 6.693 (d, 1H, J=15.9 Hz, CH), 6.687 (d, 2H, J=9.3 Hz, phenyl protons), 4.60 (broad, 1H, CH₂), 3.078 (s, 3H, CH₃), 3.070 (s, 3H, CH₃), 2.220 (s, 3H, CH₃), 1.80 (broad, 1H, CH₂)

Compound Obtained in Example 7

NMR (CDCl₃): 7.991 (dd, 2H, J=8.0, 1.5 Hz, phenyl protons), 7.505 (d, 1H, J=15.9 Hz, CH), 7.486 (d, 2H, J=9.0 Hz, phenyl protons), 7.376 (m, 3H, phenyl protons), 6.632 (d, 2H, J=9.0 Hz, phenyl protons), 6.591 (d, 1H, J=15.66 Hz, CH), 3.065 (s, 3H, CH₃), 3.040 (s, 3H, CH₃), 5.25 (broad, 1H, CH₂), 1.85 (broad, 1H, CH₂)

Compound Obtained in Example 8

NMR (CDCl₃): 7.448 (d, 2H, J=8.7 Hz, phenyl protons), 7.436 (d, 1H, J=15.9H, CH), 6.680 (d, 2H, J=8.7 Hz, phenyl protons), 6.668 (d, 1H, J=15.9 Hz, CH), 4.57 (broad, 1H, CH₂), 3.432 (q, 4H, J=7.2 Hz, 2CH₂), 1.83 (broad, 1H, CH₂), 1.587 (s, 3H, CH₃), 1.212 (t, 6H, J=7.2 Hz, 2CH₃)

Compound Obtained in Example 9

NMR(CDCl₃): 7.994 (d, 2H, J=8.1 Hz, phenyl protons), 7.502 (m, 3H, phenyl protons), 7.496 (d, 1H, J=15.9 Hz, CH), 7.357 (d, 2H, J=8.7 Hz, phenyl protons), 6.606 (d, 2H, J=8.7 Hz, phenyl protons), 6.577 (d, 1H, J=15.6 Hz, CH), 5.30 (broad, 1H, CH₂), 3.404 (q, 4H, J=7.2 Hz, 2CH₂), 1.95 (broad, 1H, CH₂), 1.186 (t, 6H, J=7.2 Hz, 2CH₃)

Compound Obtained in Example 10

NMR (CDCl₃): 7.354 (d, 1H, J=15.9 Hz, CH), 7.037 (s, 2H, phenyl protons), 6.609 (d, 1H, J=15.9 Hz, CH), 4.51 (broad, 1H, CH₂), 3.289 (t, 4H, J=6.0 Hz, 2CH₂), 2.737 (t, 4H, J=6.0 Hz, 2CH₂), 2.182 (s, 3H, CH₃), 1.962 (quin, 4H, J=6.0 Hz, 2CH₂), 1.80 (broad, 1H, CH₂)

Compound Obtained in Example 11

NMR (CDCl₃): 7.975 (dd, 2H, J=6.6 Hz, phenyl protons), 7.48 (m, 3H, phenyl protons), 7.422 (d, 1H, J=15.6 Hz, CH), 6.948 (s, 2H, phenyl protons), 6.526 (d, 1H, J=15.6 Hz, CH), 5.23 (broad, 1H, CH₂), 3.259 (t, 4H, J=5.7 Hz, 2CH₂), 2.702 (t, 4H, J=6.5 Hz, 2CH₂), 1.932 (quin, 4H, J=5.7 Hz, 2CH₂), 1.93 (broad, 1H, CH₂)

Example 12

The object compound 2,3-dicyano-5-phenyl-7-(2-(9-ethyl-3-carbazolyl)vinyl-6H-1-yl)-1,4-diazepine (compound 12) was obtained in the same manner as in Example 5 with the exception that 9-ethylcarbazol)-3-yl-carbaldehyde was used in lieu of 4-methoxybenzaldehyde. The absorption spectrum and fluorescence spectrum of the compound (12) thus obtained were measured as in Example 1. The peak wavelength in the absorption spectrum was 461 nm and that in the fluorescence spectrum was 572 nm, the difference between which was 111 nm.

Compound 12

NMR (d₆-DMSO): 8.573 (s, 1H, phenyl proton), 8.270 (d, 2H, J=7.5 Hz, phenyl protons), 8.184 (d, 1H, J=7.8 Hz, phenyl proton), 8.180 (d, 1H, J=16.2 Hz, CH), 7.820 (d, 1H, J=8.7 Hz, phenyl proton), 7.661 (d, 1H, J=9.0 Hz, phenyl proton), 7.659 (d, 1H, J=9.0 Hz, phenyl proton), 7.580 (m, 3H, phenyl), 7.507 (t, 1H, J=7.8 Hz, phenyl proton), 7.276 (t, 1H, J=7.5 Hz, phenyl proton), 7.146 (d, 1H, J=16.2 Hz, CH), 5.85 (broad, 1H, CH₂), 4.461 (q, 2H, J=7.2 Hz, CH₂), 2.267 (broad, 1H, CH₂), 1.305 (t, 3H, J=6.9 Hz, CH₃)

Example 13

The object compound 2,3-dicyano-5-methyl-7-(2-(3-indolyl)vinyl-1-yl)-6H-1,4-diazepine (compound 13) represented by the formula (vii) was obtained in the same manner as in Example 5 with the exception that a compound represented by the following formula (vi) was used in lieu of 4-methoxybenzaldehyde.

(vi)

(vii)

Compound 13

NMR (d$_6$-DMSO): 12.032 (s, 1H, NH), 8.157 (d, 1H, J=15.9 Hz, CH), 8.082 (d, 1H, J=2.1 Hz, pyrrole proton), 8.034 (d, 1H, J=7.8 Hz, phenyl proton), 7.492 (d, 1H, J=7.2 Hz, phenyl proton), 7.231 (m, 2H, phenyl protons), 6.926 (d, 1H, J=16.2 Hz, CH), 5.00 (broad, 1H, CH$_2$), 2.10 (broad, 1H, CH$_2$), 2.194 (s, 3H, CH$_3$)

Example 14

The object compound 2,3-dicyano-5-phenyl-7-(2-(3-indolyl)vinyl-1-yl)-6H-1,4-diazepine represented by the formula (viii) was obtained in the same manner as in Example 5 with the exception that benzylacetone and an aldehyde represented by the formula (vi) in lieu of acetylacetone and 4-methoxybenzaldehyde, respectively.

(viii)

Compound Obtained in Example 14

NMR (d$_6$-DMSO): 12.004 (broad, 1H, NH), 8.259 (d, 2H, J=7.5 Hz, phenyl protons), 8.173 (d, 1H, J=15.9 Hz, CH), 8.037 (s, 1H, pyrrole proton), 7.990 (m, 1H, phenyl protons), 7.54 (m, 3H, phenyl protons), 7.485 (m, 1H, phenyl proton), 7.226 (m, 2H, phenyl protons), 6.901 (d, IH, J=15.9 Hz, CH), 5.822 (broad, 1H, CH$_2$), 2.189 (broad, 1H, CH$_2$)

[Comparison of the Absorption Spectra and the Fluorescence Spectra of the Compounds (I) (II)]

Figure 1:
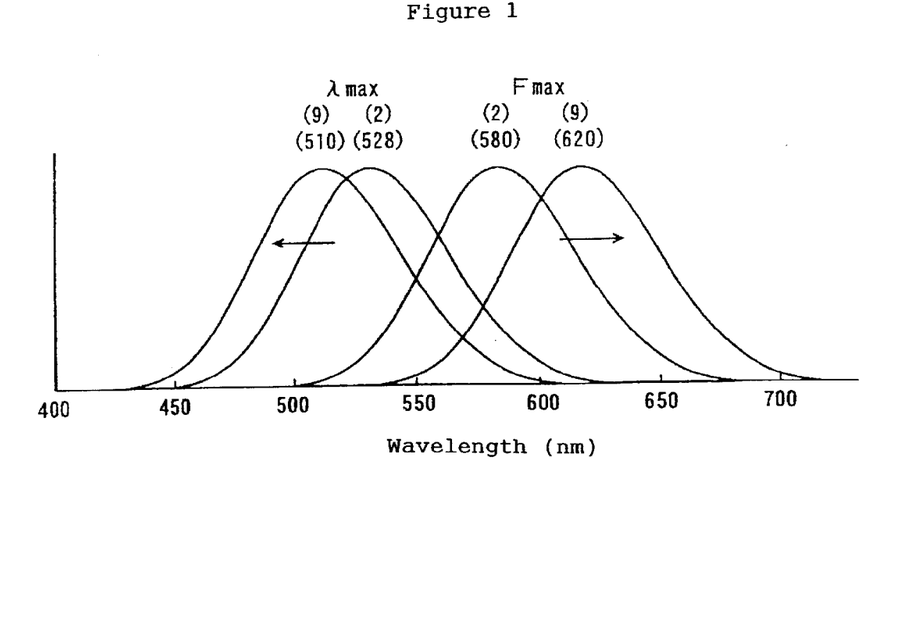
FIG. 1 shows the absorption spectra and the fluorescence spectra of the compounds obtained in Examples 2 and 9.

FIG. 1 is a graph showing the absorption spectra (peak wavelength λmax) and the fluorescence spectra (peak wavelength λmax) of the compounds represented by the following formulae of Example 2 (corresponding to Compound (I)) and Example 9 (corresponding to compounds (II)) overlapped. As is obvious from FIG. 1, the fluorescence wavelength of the compound of the present invention was different for different substituents. Compared to the compound of Example 2, the absorption maximum wavelength of the compound of Example 9 shifted toward shorter wavelengths, and the fluorescence maximum wavelength shifted toward longer wavelengths.

Compound (2) of Example 2

Compound (9) of Example 9

[Organic Electroluminescence Device]

Example 15

A coating fluid was prepared by dissolving 100.2 mg of poly-N-vinylcarbazol (PVK: Kanto Kagaku K.K.), 99.6 mg of 2-(4-biphenyl)-5-(4-tert-butylphenyl)-1,3,4-oxadiazol (PBD: Aldrich Chemical Company, Inc.), and 0.5 mg of the compound (4) obtained in Example 4 in 8 ml of toluene. After forming a film of indium-tin-oxide (ITO) on a glass substrate, the coating fluid was applied on the ITO film by spin coating to form an organic layer of 80 nm thick. Thereafter, on the organic layer, an Al/Li electrode of 200 nm thick (manufactured by Kojundo Kagaku, K.K.; Li content 0.78% by weight) was made by vacuum deposition to give an organic electroluminescence device.

Figure 2:
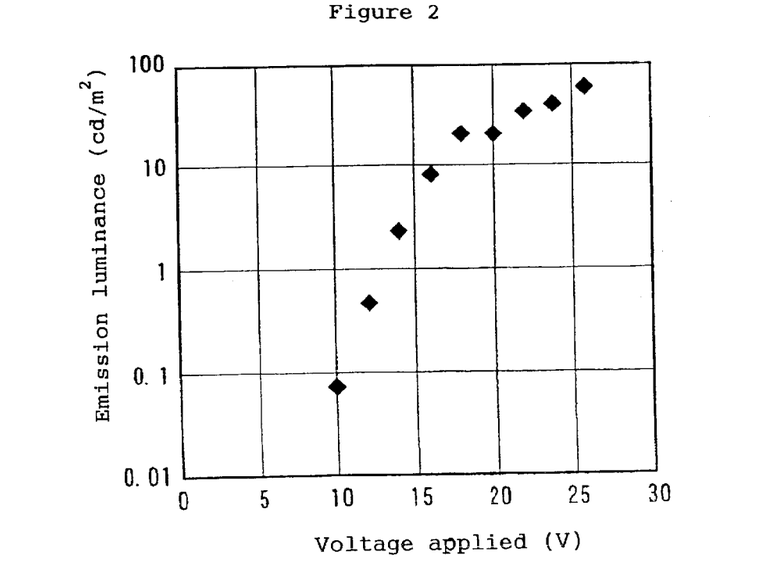
FIG. 2 is a graph showing the emission luminance of the organic electroluminescence device obtained in Example 15 versus voltage applied thereto.

With the ITO electrode of the organic electroluminescence device obtained as anode and the AL/Li electrode as cathode, a direct current was applied between the both electrodes in the atmosphere thereby to make the device emit light. The peak wavelength of the emission spectrum was 549 nm (measured by a multichannel analyzer PMA-11 manufactured by Hamamatsu Photonics, K.K.,). The emission luminance was measured using a luminance detecting device LS-110 manufactured by Minolta. FIG. 2 is a graph showing the value of luminance versus voltage applied.

Examples 16 and 17

Figure 3:
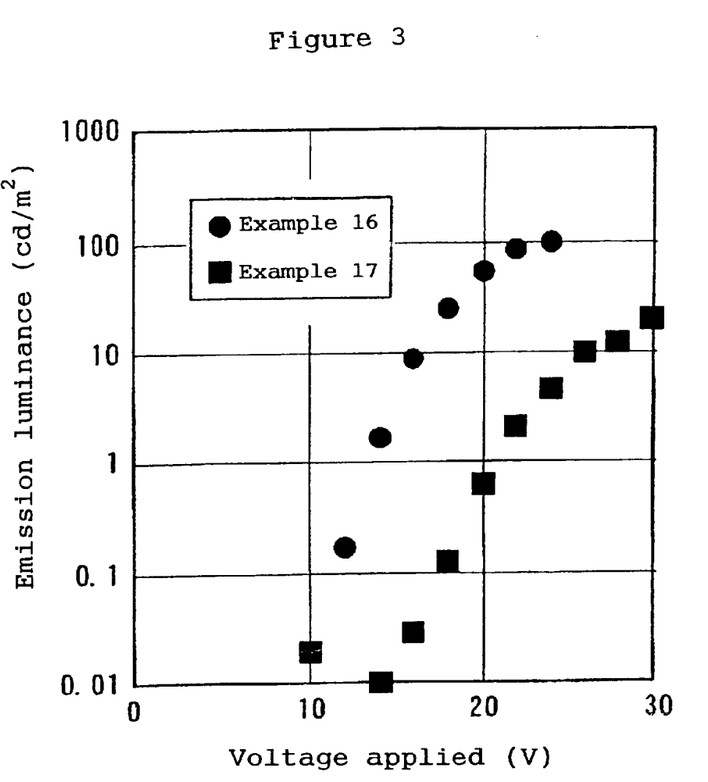
FIG. 3 is a graph showing the emission luminance of the organic electroluminescence devices obtained in Examples 16 and 17 versus voltage applied thereto.

An organic EL device was fabricated in the same manner as in Example 15 with the exception that 100 mg of PVK, 100 mg of PBD, and 0.5 mg of the compound (10) obtained in Example 10 (Example 16) or 1.1 mg of the compound (11) obtained in Example 11 (Example 17) as an emission center compound were used, and then its emission spectrum and luminance were measured. The thickness of the organic layer of each organic EL device obtained was 83 nm (Example 16) and 100 nm (Example 17). The peak wavelengths in the emission spectra were individually 614 nm (Example 16) and 663 nm (Example 17). FIG. 3 is a graph showing the value of emission luminance versus voltage applied.

What is claimed is:

1. A nitrogen-containing heterocyclic compound represented by the following formula (I) or (II):

(I)

(II)

wherein $X^1$ and $X^2$ are the same or different, each representing a hydrogen atom, an alkyl group, or an electron attractive group and at least one of which being an electron attractive group; $R^1$ and $R^2$ are the same or different, each representing a hydrogen atom, an alkyl group, an aryl group, an aralkyl group, or an alkoxy group; and the ring Z represents a hydrocarbon ring which may have a substituent or a heterocycle which may have a substituent.

2. A nitrogen-containing heterocyclic compound according to claim 1, wherein the electron attractive group is at least one member selected from the group consisting of cyano group, an acyl group, and an alkoxy group.

3. A nitrogen-containing heterocyclic compound according to claim 1, wherein at least one of the groups $X^1$ and $X^2$ is a cyano group.

4. A nitrogen containing heterocyclic compound according to claim 1, wherein $R^1$ and $R^2$ are the groups selected from the group consisting of an alkyl group, an aryl group, and an aralkyl group.

5. A nitrogen-containing heterocyclic compound according to claim 1, wherein the hydrocarbon ring or the heterocycle of the ring Z is an aromatic ring.

6. A nitrogen-containing heterocyclic compound according to claim 1, wherein the substituent of the ring Z is at least one member selected from the group consisting of an alkyl group, a cycloalkyl group, an aryl group, an arylalkyl group, a halogen atom, hydroxyl group, an alkoxy group, a hydroxyalkyl group, carbonyl group, carboxyl group, an alkoxycarbonyl group, an alkylcarbonyl group, an alkoxycarbonyl group, an alkylcarbonyl group, an arylcarbonyl group, an acyloxy group, cyano group, amino group, an N-substituted amino group, nitro group, and sulfonyl group.

7. A nitrogen-containing heterocyclic compound according to claim 1, which is capable of emitting light by being irradiated with light.

8. A nitrogen-containing heterocyclic compound according to claim 7, which is capable of emitting fluorescent light by being irradiated with light.

9. A nitrogen-containing heterocyclic compound according to claim 7, wherein the wavelength of light emitted by the compound is 380 to 800 nm.

10. A nitrogen-containing heterocyclic compound according to claim 1, which is capable of emitting light by the action of an electric field.

11. A process for producing a nitrogen-containing heterocyclic compound represented by the following formula (I) or (II):

(I)

(II)

wherein $X^1$ and $X^2$ are the same or different, each representing a hydrogen atom, an alkyl group, or an electron attractive group and at least one of which being an electron attractive group; $R^1$ and $R^2$ are the same or different, each representing a hydrogen atom, an alkyl group, an aryl group, an aralkyl group, or an alkoxy group; and the ring Z is a hydrocarbon ring which may have a substituent, or a heterocylcle which may have a substituent which comprises reacting a compound represented by the following formula ($I_a$) or ($II_a$):

($I_a$)

($II_a$)

wherein the $X^1$, $X^2$, $R^1$, and $R^2$ have the same meanings as defined above with a compound represented by the following formula (III):

(III)

wherein the ring Z has the same meaning as defined above.

12. An organic electroluminescence device, which comprises a pair of electrodes and an organic layer interposed therebetween, wherein the organic layer contains a compound represented by the formula (I) or (II) recited in claim 1.

13. An organic electroluminescence device according to claim 12, wherein the organic layer has a light-emitting layer comprising a compound represented by the formula (I) or (II).

14. An organic electroluminescence device according to claim 13, wherein the organic layer has (1) a single layer structure composed of a light-emitting layer having at least one function selected from an electron-transporting function and a hole-transporting function, or (2) a layered structure composed of a layer having at least one function selected from an electron-transporting function and a hole-transporting function, and a light-emitting layer.

15. An organic electroluminescence device according to claim 12, wherein the organic layer comprises a compound represented by the formula (I) and (II) and an organic polymer having at least one function selected from an electron-transporting function and a hole-transporting function.

* * * * *